United States Patent
Eller et al.

(10) Patent No.: US 6,198,002 B1
(45) Date of Patent: Mar. 6, 2001

(54) PREPARATION OF SECONDARY AND TERTIARY 2-METHYL-1, 5-PENTANEDIAMINES

(75) Inventors: Karsten Eller, Ludwigshafen; Bernd Fiege, Frankenthal; Stefan Rittinger, Mannheim; Eberhard Fuchs, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/324,715

(22) Filed: Jun. 3, 1999

(30) Foreign Application Priority Data

Jun. 6, 1998 (DE) .............................. 198 25 452

(51) Int. Cl.$^7$ .................................. C07C 209/48
(52) U.S. Cl. ..................... 564/491; 564/469; 564/492
(58) Field of Search ................... 564/469, 491, 564/492

(56) References Cited

U.S. PATENT DOCUMENTS

| | | |
|---|---|---|
| 3,673,251 | 6/1972 | Frampton . |
| 5,463,130 | 10/1995 | Witzel . |
| 5,557,011 | 9/1996 | Witzel . |
| 5,698,607 | 12/1997 | Heveling et al. . |

FOREIGN PATENT DOCUMENTS

| | | |
|---|---|---|
| 19713 383 | 10/1998 | (DE) . |
| 673 918 | 9/1995 | (EP) . |
| 1157637 | 7/1969 | (GB) . |
| 1157638 | 7/1969 | (GB) . |
| 95/30666 | 11/1995 | (WO) . |
| 96/33986 | 10/1996 | (WO) . |

OTHER PUBLICATIONS

Catalytic Hydrogenation, Hydrogenation of Nitriles, Volf et al., Chapter 4, 105–145, 1986.

*Primary Examiner*—Shailendra Kumar
(74) *Attorney, Agent, or Firm*—Keil & Weinkauf

(57) ABSTRACT

A process for preparing a secondary or tertiary 2-methyl-1, 5-pen-tanediamine of the formula I

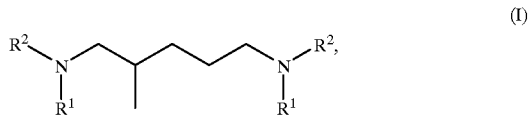

(I)

where
$R^1$ and $R^2$ are H, $C_1$–$C_{20}$-alkyl, $C_3$–$C_8$-cycloalkyl, aryl, $C_7$–$C_{20}$-arylalkyl,
where the radicals $R^1$ and $R^2$ may bear substituents selected from the group consisting of $C_1$–$C_{20}$-alkyl, $C_1$–$C_{20}$-alkoxy, $C_6$–$C_{20}$-aryloxy and hydroxy, and $R^1$ and $R^2$ are not simultaneously hydrogen,
or
$R^1$ and $R^2$ are together an unsubstituted or $C_1$–$C_{20}$-alkyl- and/or $C_1$–$C_{20}$-alkoxy-substituted $C_3$–$C_7$-alkylene chain which may, if desired, be interrupted by one or two O or $NR^3$ groups, where
$R^3$ is H or $C_1$–$C_{20}$-alkyl
comprises reacting 2-methylglutarodinitrile with a primary or secondary amine of the formula $R^1R^2NH$ and hydrogen at from 50 to 250° C. and pressures of from 0.5 to 35 MPa in the presence of an oxidic supported catalyst comprising one or more noble metals which has been treated with hydrogen at from 50 to 300° C. for at least 0.5 hour before use. The compound 1,5-bis (dimethylamino)-2-methylpentane is also claimed.

6 Claims, No Drawings

PREPARATION OF SECONDARY AND TERTIARY 2-METHYL-1,5-PENTANEDIAMINES

The present invention relates to a process for preparing secondary and tertiary 2-methyl-1,5-pentanediamines of the formula I

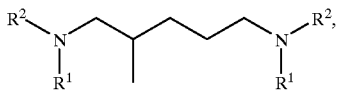

where
R$^1$ and R$^2$ are H, C$_1$–C$_{20}$-alkyl, C$_3$–C$_8$-cycloalkyl, aryl, C$_7$–C$_{20}$-arylalkyl,
where the radicals R$^1$ and R$^2$ may bear substituents selected from the group consisting of C$_1$–C$_{20}$-alkyl, C$_1$–C$_{20}$-alkoxy, C$_6$–C$_{20}$-aryloxy and hydroxy, and R$^1$ and R$^2$ are not simultaneously hydrogen,
or
R$^1$ and R$^2$ are together an unsubstituted or C$_1$–C$_{20}$-alkyl- and/or C$_1$–C$_{20}$-alkoxy-substituted C$_3$–C$_7$-alkylene chain which may, if desired, be interrupted by one or two O or NR$^3$ groups, where
R$^3$ is H or C$_1$–C$_{20}$-alkyl.

The invention further relates to the compound 1,5-bis(dimethylamino)-2-methylpentane.

U.S. Pat. No. 3,673,251 describes a continuous process for preparing secondary and/or tertiary monoamines, diamines or polyamines from mononitriles, dinitriles or polynitriles and primary or secondary amines. In the preparation of N,N,N',N'-tetraethyl-2-methyl-1,5-pentanediamine (loc. cit., Example 3), a yield of 60% is achieved in a complicated process using 5% palladium on carbon and diatomaceous earth as catalyst with adsorption of the ammonia formed on solid calcium chloride.

WO 95/30666 discloses the self-condensation of three molecules of 2-methylglutarodinitrile in the presence of hydrogen over Pd/Al$_2$O$_3$ catalysts to give 1,5-bis(3-methylpiperidino)-2-methylpentane. However, this process cannot be applied to the preparation of other tertiary or secondary 2-methyl-1,5-pentanediamines. Example 8 of this patent application describes the reaction of excess 3-methylpiperidine with 2-methylglutarodinitrile and hydrogen in the presence of a Pd/Al$_2$O$_3$ catalyst, which gives 1,5-bis(3-methylpiperidino)-2-methylpentane as main product. Before the reaction, the reaction temperature of 180° C. had been set in a very small reactor charged with catalyst (amount of catalyst: 3 g) in a stream of hydrogen under pressure.

WO 96/33986 describes the reaction of 2-methylglutarodinitrile with 3-methylpiperidine and hydrogen over a Pd/Al$_2$O$_3$ catalyst to give a mixture of 2- and 4-methyl-5-(3-methylpiperidino)-pentanenitrile which is hydrogenated in a separate step to form 2- and 4-methyl-5-(3-methylpiperidino)pentane-1-amine. The corresponding tertiary diamine, viz. 1,5-bis(3-methylpiperidino)-2-methylpentane is obtained only as by-product in yields of not more than 24.4% (loc. cit., Example 1). Prior to the reaction, the very small reactor charged with catalyst (amount of catalyst: 3 g) had been heated to the reaction temperature of 150° C. in a stream of hydrogen under pressure.

GB-A-1, 157,637, GB-A-1, 157,638 and GB-A-1, 157,639 disclose the reaction of 2-methylglutarodinitrile with diethylamine in the presence of hydrogen and palladium to give 5-diethylamino-2-methylvaleronitrile. Despite long reaction times and high molar excesses of diethylamine, no N,N,N',N'-tetraethyl-2-methyl-1,5-pentanediamine was found here.

According to EP-A-673 918, nitriles are reacted with secondary amines and hydrogen in the presence of palladium catalysts to give peralkylated amines. Here, 3-dimethylaminopropionitrile and dimethylamine are reacted to form N,N,N',N'-tetramethyl-propylene-1,3-diamine, 3-hydroxypropionitrile and dimethylamine are reacted to form 3-dimethylaminopropan-1-ol and piperazine is reacted with acetonitrile to give N-ethylpiperazine.

EP-A-599 180 describes a process for preparing N,N,N',N'-tetrasubstituted diamines by reaction of dinitriles with secondary amines. Here, adiponitrile is reacted with dimethylamine and hydrogen in the presence of a Pd/Al$_2$O$_3$-catalyst to give N,N,N',N'-tetramethylhexamethylenediamine (loc. cit., Examples 1 to 6).

An attempt to apply the process of EP-A-599 180 to the preparation of N,N,N',N'-2-pentamethylpentane-1,5-diamine from 2-methylglutarodinitrile and dimethylamine gives only unsatisfactory yields.

A dependence of the results of the reaction of nitrites with amines and hydrogen in the presence of catalysts comprising noble metal on the molecular structure of the nitrile used is mentioned in L. Cerveny, Studies in Surface Science and Catalysis, Vol. 27: Catalytic Hydrogenation, page 122, lines 1–4 (Elsevier, 1986).

The earlier German Patent Application No. 197 13 383.5 describes an improved, compared to EP-A-673 918 and EP-A-599 180, process (cf. loc. cit., page 2, lines 1–2) for preparing tertiary amines from nitrites and secondary amines and hydrogen in the presence of a palladium-containing catalyst. In the example, N,N,N',N'-tetramethylhexamethylenediamine is prepared from adiponitrile and dimethylamine using an improved catalyst comprising palladium and platinum on zirconium dioxide.

L. Cerveny, Studies in Surface Science and Catalysis, Vol. 27: Catalytic Hydrogenation teaches, on page 124, last paragraph, page 125, first paragraph and page 140, Chapter 4.7, lines 10–11, that the nature of the support of the noble metal catalyst in the reaction of nitrites with amines has only a slight effect on the catalyst properties. According to loc. cit., page 122, second-last paragraph, pretreatment of a supported palladium catalyst with hydrogen at 200° C. makes it inactive in the catalytic reaction of nitrites to give primary, secondary or tertiary amines.

It is an object of the invention to find an economical process which allows secondary and tertiary 2-methyl-1,5-pentanediamines to be obtained in good yields and selectivities and at long catalyst operation lives from 2-methylglutarodinitrile and primary or secondary amines.

A further object is the preparation of 1,5-bis(dimethylamino)-2-methylpentane.

We have found that this object is achieved by a process for preparing a secondary or tertiary 2-methyl-1,5-pentanediamine of the formula I

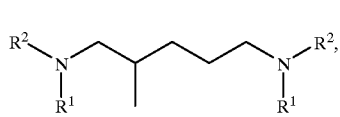

where R$^1$ and R$^2$ are as defined at the outset, which comprises reacting 2-methylglutarodinitrile

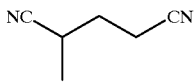

with a primary or secondary amine of the formula $R^1R^2NH$ and hydrogen at from 50 to 250° C. and pressures of from 0.5 to 35 MPa in the presence of an oxidic supported catalyst comprising one or more noble metals which has been treated with hydrogen at from 50 to 300° C. for at least 0.5 hour before use.

We have also found 1,5-bis(dimethylamino)-2-methylpentane.

The radicals $R^1$ and $R^2$ independently have the following meanings, where $R^1$ and $R^2$ are not simultaneously hydrogen:

hydrogen (H), $C_1$–$C_{20}$-alkyl, preferably $C_1$–$C_{12}$-alkyl, for example methyl, ethyl, n-propyl, iso-propyl, n-butyl, iso-butyl, sec-butyl, tert-butyl, n-pentyl, iso-pentyl, sec-pentyl, neo-pentyl, 1,2-dimethylpropyl, n-hexyl, iso-hexyl, sec-hexyl, cyclopentylmethyl, n-heptyl, iso-heptyl, cyclohexylmethyl, n-octyl, 2-ethylhexyl, n-nonyl, iso-nonyl, n-decyl, iso-decyl, n-undecyl, n-dodecyl, iso-dodecyl, preferably $C_1$–$C_4$-alkyl such as methyl, ethyl, n-propyl, iso-propyl, n-butyl, iso-butyl, sec-butyl and tert-butyl, particularly preferably methyl, $C_3$–$C_8$-cycloalkyl such as cyclopropyl, cyclobutyl, cyclopentyl, cyclohexyl, cycloheptyl and cyclooctyl, preferably cyclopentyl, cyclohexyl and cyclooctyl, particularly preferably cyclopentyl and cyclohexyl, aryl, preferably $C_6$–$C_{20}$-aryl, for example phenyl, 1-naphthyl, 2-naphthyl, 1-anthryl, 2-anthryl, 9-anthryl, particularly preferably phenyl, 1-naphthyl and 2-naphthyl, very particularly preferably phenyl, $C_7$–$C_{20}$-arylalkyl such as benzyl, 1-phenylethyl, 2-phenylethyl, 1-naphthylmethyl, 2-naphthylmethyl, phenanthrylmethyls, 4-tert-butylphenylmethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenylethyl and 2-phenylethyl, where in these cases the radicals $R^1$ and $R^2$ may, independently of one another, bear substituents which are inert under the reaction conditions, e.g. $C_1$–$C_{20}$-alkyl, $C_1$–$C_{20}$-alkoxy, $C_6$–$C_{20}$-aryloxy and hydroxy.

The number of such substituents in $R^1$ and $R^2$ can be, depending on the type of radical, from 0 to 5, preferably from 0 to 3, in particular 0, 1 or 2. Suitable substituents are:

$C_1$–$C_{20}$-alkyl, as defined above, $C_1$–$C_{20}$-alkoxy, preferably $C_1$–$C_8$-alkoxy, for example methoxy, ethoxy, n-propoxy, iso-propoxy, n-butoxy, iso-butoxy, sec-butoxy, tert-butoxy, n-pentoxy, iso-pentoxy, sec-pentoxy, neo-pentoxy, 1,2-dimethylpropoxy, n-hexoxy, iso-hexoxy, sec-hexoxy, n-heptoxy, iso-heptoxy, n-octoxy, iso-octoxy, particularly preferably $C_1$–$C_4$-alkoxy, such as methoxy, ethoxy, n-propoxy, iso-propoxy, n-butoxy, iso-butoxy, sec-butoxy and tert-butoxy, $C_6$–$C_{20}$-aryloxy such as phenoxy, 1-naphthoxy and 2-naphthoxy, preferably phenoxy, hydroxy (—OH).

Furthermore, apart from the above definition, the radicals $R^1$ and $R^2$ can also together be a $C_3$–$C_7$-alkylene chain, for example —(CH$_2$)$_3$—, —(CH$_2$)$_4$—, —(CH$_2$)$_5$—, —(CH$_2$)$_6$—, —(CH$_2$)$_7$—, preferably —(CH$_2$)$_4$— and —(CH$_2$)$_5$—, which may, if desired, be interrupted by one or two O or $NR^3$ groups, for example —(CH$_2$)—O—(CH$_2$)$_2$—, —(CH$_2$)—NR$^3$—(CH$_2$)$_2$—, —(CH$_2$)$_2$—O—(CH$_2$)$_2$—, —(CH$_2$)$_2$—NR$^3$—(CH$_2$)$_2$—, —CH$_2$—O—(CH$_2$)$_3$—, —CH$_2$—NR$^3$—(CH$_2$)$_3$—, preferably —(CH$_2$)$_2$—O—(CH$_2$)$_2$— and —(CH$_2$)$_2$—NR$^3$—(CH$_2$)$_2$—, and may additionally bear one or two substituents which are inert under the reaction conditions, for example $C_1$–$C_{20}$-alkyl and/or $C_1$–$C_{20}$-alkoxy, where $C_1$–$C_{20}$-alkyl and $C_1$–$C_{20}$-alkoxy are as defined above, for example —CH$_2$—CHCH$_3$—O—CHCH$_3$—CH$_2$—, —(CH$_2$)$_2$—CH(OCH$_3$)—(CH$_2$)$_2$—, —(CH$_2$)$_2$—CH(OC$_2$H$_5$)—(CH$_2$)$_2$—, —(CH$_2$)—CHCH$_3$—(CH$_2$)$_2$—, —(CH$_2$)$_2$—CHCH$_3$—(CH$_2$)$_2$—, —CH$_2$—CHCH$_3$—(CH$_2$)$_3$—, —(CH$_2$)—CHCH$_3$—(CH$_2$)$_2$—.

The radical $R^3$ has the following meanings:

hydrogen (H), $C_1$–$C_{20}$-alkyl, as defined above.

The process can be carried out as follows:

To prepare tertiary amines of the formula $R^1R^2N$—CH$_2$—CHCH$_3$—(CH$_2$)$_3$—NR$^1R^2$, 2-methylglutarodinitrile is reacted with a secondary amine of the formula $R^1R^2NH$ in the presence of hydrogen and an oxidic supported catalyst comprising one or more noble metals by the process as claimed in claim 1.

To prepare secondary amines of the formula $R^1HN$—CH$_2$—CHCH$_3$—(CH$_2$)$_3$—NHR$^1$, 2-methylglutarodinitrile is reacted with a primary amine of the formula $R^1NH_2$ (i.e. $R^2$ is H in this case) in the presence of hydrogen and an oxidic supported catalyst comprising one or more noble metals by the process as claimed in claim 1.

According to the present invention, the supported catalyst is treated with hydrogen prior to being used for the amination of the nitrile. This is achieved, for example, by passing hydrogen gas or a hydrogen-containing stream of inert gas (e.g. nitrogen, argon) over the supported catalyst after it has been installed in the reactor. Pure hydrogen gas is preferred here.

During the treatment of the catalyst with hydrogen, each of the starting materials 2-methylglutarodinitrile and primary or secondary amine is absent.

The treatment of the supported catalyst with hydrogen is generally carried out at pressures of from 0.1 to 35 MPa. It can also be carried out at higher pressures, e.g. 50 MPa, but this requires an unnecessarily high outlay in terms of apparatus. Preference is given to pressures of from 0 to 25 MPa, particularly preferably from 0 to 20 MPa.

The treatment of the supported catalyst with hydrogen is generally carried out at from 50 to 300° C., preferably from 80 to 250° C., particularly preferably from 100 to 200° C. and very particularly preferably from 130 to 160° C.

In many cases it is practical to carry out the treatment of the supported catalyst with hydrogen in the reactor in which the later amination reaction is also carried out and at the pressures and temperatures which are employed later in this reaction.

The time for which the supported catalyst is treated with hydrogen is at least 0.5 hour, preferably at least 2 hours, particularly preferably at least 3 hours. Treatment times of more than 2 days generally result in no further improvements in the catalyst properties.

Depending on the temperature selected and the hydrogen pressure selected, the time for which the supported catalyst is treated with hydrogen is generally in the range from 0.5 to 48 hours, preferably from 2 to 24 hours.

For example, at hydrogen pressures of from 0 to 25 MPa and temperatures of from 100 to 200° C., the treatment time can be from 2 to 24 hours, preferably from 4 to 12 hours. In general, the treatment times required decrease with increasing pressure and increasing temperature.

Suitable catalysts for the process of the present invention comprise one or more noble metals on oxidic supports. As noble metals, it is possible to use, in particular, silver, rhenium, ruthenium, palladium, platinum, rhodium, osmium or iridium. Preference is given to palladium, platinum and ruthenium, and particular preference is given to the simultaneous use of palladium and platinum.

The total amount of noble metals, calculated as total amount of noble metals in the oxidation state 0, in the supported catalyst is from 0.01 to 10% by weight, preferably from 0.01 to 3% by weight, particularly preferably from 0.01 to 1.5% by weight, based on the total weight of the catalyst.

In general, the catalysts contain from 0.01 to 5% by weight, preferably from 0.01 to 1% by weight, of each noble metal. Preference is given to catalysts containing from 0.1 to 1% by weight of palladium. Particular preference is given to catalysts containing 0.1 to 1% by weight of palladium and, in addition, from 0.01 to 1% of platinum.

In addition to the noble metals, the catalysts can also be doped with other metals, for example with other transition metals or lanthanides.

Suitable catalysts have been described, for example, in EP-A-599 180, EP-A-673 918 and the German Patent Application No. 197 13 383.5.

As supports, it is possible to use, in particular, all oxidic supports. Preference is given to γ- or α-aluminum oxide, silicon dioxide, titanium dioxide, zirconium dioxide, cerium dioxide, $Al_2O_3$, $SiO_2$, $TiO_2$ or $ZrO_2$ doped with alkali metal oxides or alkaline earth metal oxides, or mixtures of these support materials. Particular preference is given to aluminum oxide and zirconium dioxide. Very particular preference is given to zirconium dioxide. The supports can be used in any form, for example as powder, extrudates, pellets, spheres or rings. The production of the supports and the application of the noble metal components can be carried out by customary methods, as described, for example, in EP-A-599 180 and EP-A-673 918.

As an example, only impregnation with a solution of the noble metals in the form of their nitrates, acetates or chlorides followed by drying, calcination and possibly reduction will be mentioned here. When a plurality of noble metals are applied, the impregnation can be carried out simultaneously or successively in any order.

In the process of the present invention, the two starting materials 2-methylglutarodinitrile and primary or secondary amine are usually used in a molar ratio of from 1:2 to 1:40, preferably from 1:3 to 1:20, particularly preferably from 1:4 to 1:15. However, it is also possible to use larger excesses of amine, since in general the unreacted amine can easily be recirculated owing to the different boiling points.

Examples of primary amines which can be used are methylamine, ethylamine, n- and i-propylamine, n-butylamine, i-butylamine, tert-butylamine, n-pentylamine, i-pentylamine, neo-pentylamine, n-hexylamine, 2-ethylhexylamine, cyclopropylamine, cyclopentylamine, cyclohexylamine, 2-methylpentylamine, 2-methylhexylamine, 4-methylhexylamine, aniline, 2,6-dimethylaniline, ethanolamine and 2-phenoxyethylamine. Preference is given to methylamine, ethylamine, n-propylamine, i-propylamine, and cyclohexylamine, particularly preferably methylamine and ethylamine.

Examples of secondary amines which can be used are dimethylamine, diethylamine, methylethylamine, di-n-propylamine, diisopropylamine, di-n-butylamine, diisobutylamine, di-s-butylamine, ethylisopropylamine, bis(2-ethylhexyl)amine, dicyclohexylamine, methylcyclohexylamine, diphenylamine, N-ethylaniline, diethanolamine, pyrrolidine, piperidine, 2-methylpiperidine, 3-methylpiperidine, morpholine, piperazine, 1-methylpiperazine and 1-ethylpiperazine. Preference is given to dimethylamine, diethylamine, di-n-butylamine, piperidine and morpholine, particular preference is given to dimethylamine and diethylamine. Very particular preference is given to dimethylamine.

The reaction of 2-methylglutarodinitrile with the primary or secondary amine can be carried out continuously or batchwise. In a batchwise procedure, e.g. in a pressure autoclave, the reactor is, for example, charged with the starting materials together with the supported catalyst which has previously been treated with hydrogen as described above, hydrogen is injected and the contents of the reactor are then brought to the reaction temperature. After the reaction is complete, the reaction vessel is vented and the contents are worked up. The catalyst can here be used as powder or, in a suitable apparatus, also in the form of extrudates, pellets, etc.

The reaction is preferably carried out continuously in a cascade of pressure vessels or in a reactor in which the catalyst is located as a fixed bed, e.g. a tube reactor. The space velocity over the catalyst is usually in the range from 0.05 to 1 $l_{nitrile} \cdot l_{cat.}^{-1} \cdot h^{-1}$, preferably in the range from 0.1 to 0.8 $l_{nitrile} \cdot l_{cat.}^{-1} \cdot h^{-1}$.

The reaction temperature in the reaction of 2-methylglutaro-dinitrile with the primary or secondary amine depends on the reactivity of the amine and on the selected space velocity over the catalyst. Suitable reaction temperatures are in the range from 50 to 250° C., preferably from 90 to 200° C., particularly preferably from 100 to 180° C., very particularly preferably from 110 to 170° C.

The hydrogen pressure in the reaction of 2-methylglutarodinitrile with the primary or secondary amine is in the range from 0.5 to 35 MPa, preferably from 5 to 30 MPa, particularly preferably from 10 to 25 MPa.

If desired, the reaction can also be carried out in an inert solvent such as tetrahydrofuran (THF) or N-methylpyrrolidone (NMP). In this case, the 2-methylglutarodinitrile and/or the primary or secondary amine and/or ammonia formed in the reaction can be dissolved in the solvent. Preference is given to carrying out the reaction in the absence of solvent.

The secondary or tertiary amine of the formula I obtained in the process of the present invention can be separated from the reaction product and purified in a manner known per se, for example by distillation.

The amines of the formula I are important intermediates for the preparation of effect chemicals such as dyes and of active compounds and are suitable as catalysts for the preparation of polyurethanes and also as emulsifiers, plasticizers, corrosion inhibitors and textile auxiliaries.

EXAMPLES

All figures reported for product compositions are in GC-% by area.

Example 1

500 ml of a catalyst comprising 0.5% by weight of palladium on 4 mm aluminum oxide extrudates were installed in a tube reactor (length: 1450 mm, diameter: 30 mm). Reduction was carried out at 140° C. and 20 MPa of H₂ for 4 hours. Subsequently, 75 ml/h of 2-methylglutarodinitrile and 200 g/h of dimethylamine (as liquefied gas, corresponding to 294 ml/h) were passed over the catalyst in the upflow mode at 140° C. and 20 MPa hydrogen pressure (molar ratio=1:6.7). At the same time, 2.5 l/h of the output from the reactor were recirculated to the reactor (circulation mode). Under these conditions, a typical reaction product contained, after separating off ammonia and excess dimethylamine by degassing, 84.7% of N,N,N',N'-2-pentamethylpentane-1,5-diamine, 0% of 2-methylglutarodinitrile and, as by-products, 4.3% of N,N,N'-2-tetramethylpentane-1,5-diamine and N,N',N'-2-tetramethylpentane-1,5-diamine, 4.3% of N',N'-2-trimethylpentane-1,5-diamine and N,N-2-trimethylpentane-1,5-diamine and 6.7% of other compounds according to analysis by gas chromatography.

Example 2

Repetition of the procedure of Example 1 but with the reactor being operated using a single pass instead of the circulation mode gave, after separating off ammonia and excess dimethylamine, a reaction product containing 78.4% of N,N,N',N'-2-pentamethylpentane-1,5-diamine, 0% of 2-methylglutarodinitrile and, as by-products, 6.8% of N,N,N'-2-tetramethylpentane-1,5-diamine and N,N',N'-2-tetramethylpentane-1,5-diamine, 5.3% of N',N'-2-trimethylpentane-1,5-diamine and N,N-2-trimethylpentane-1,5-diamine and 9.5% of other compounds.

Example 3

500 ml of a catalyst comprising 0.9% by weight of palladium and 0.1% by weight of platinum on 4 mm zirconium dioxide extrudates were installed in a tube reactor (length: 1450 mm, diameter: 30 mm). Reduction was carried out at 140° C. using 100 l/h of H₂ at atmospheric pressure for 4 hours. Subsequently, 75 ml/h of 2-methylglutarodinitrile and 200 g/h of dimethylamine (as liquefied gas, corresponding to 294 ml/h) were passed over the catalyst in the upflow mode at 120° C. and 20 MPa hydrogen pressure (molar ratio=1:6.7). The temperature was then increased in steps to 150° C. Under these conditions, a typical reaction product contained, after separating off ammonia and excess dimethylamine, 83.4% of N,N,N',N'-2-pentamethylpentane-1,5-diamine, 0% of 2-methylglutarodinitrile and, as by-products, 5.6% of N,N,N'-2-tetramethylpentane-1,5-diamine and N,N',N'-2-tetramethylpentane-1,5-diamine, 4.3% of N',N'-2-trimethylpentane-1,5-diamine and N,N-2-trimethylpentane-1,5-diamine and 6.7% of other compounds according to analysis by gas chromatography.

Example 4

Repetition of the procedure of Example 3 but with the reaction being carried out at a reactor temperature of 160° C. gave, after separating off ammonia and excess dimethylamine, a reaction product containing 84.4% of N,N,N',N'-2-pentamethylpentane-1,5-diamine, 0% of 2-methylglutarodinitrile and, as by-products, 5.5% of N,N,N'-2-tetramethylpentane-1,5-diamine and N,N',N'-2-tetramethylpentane-1,5-diamine, 4.1% of N',N'-2-trimethylpentane-1,5-diamine and N,N-2-trimethylpentane-1,5-diamine and 6.0% of other compounds.

Example 5

Repetition of the procedure of Example 4 but with the reaction being carried out at a molar ratio of 2-methylglutaro-dinitrile:dimethylamine=1:10.1 gave no change in the yield of N,N,N',N'-2-pentamethylpentane-1, 5-diamine. The experiment was stopped after 42 days without any deactivation of the catalyst having been observed.

Example 6

500 ml of a catalyst comprising 0.5% by weight of palladium on 3 mm zirconium dioxide pellets were installed in a tube reactor (length: 1450 mm, diameter: 30 mm). Reduction was carried out at 140° C. and 20 MPa of H₂ for 10 hours. Subsequently, 75 ml/h of 2-methylglutarodinitrile and 200 g/h of dimethylamine (as liquefied gas, corresponding to 294 ml/h) were passed over the catalyst in the upflow mode at 150° C. and 20 MPa hydrogen pressure (molar ratio=1:6.7). The temperature was then increased to 160° C. Under these conditions, a typical reaction product contained, after separating off ammonia and excess dimethylamine, 76.8% of N,N,N',N'-2-pentamethylpentane-1,5-diamine, 0% of 2-methylglutarodinitrile and, as by-products, 6.6% of N,N,N'-2-tetramethylpentane-1,5-diamine and N,N',N'-2-tetramethylpentane-1,5-diamine, 5.4% N',N'-2-trimethylpentane-1,5-diamine and N,N-2-trimethylpentane-1,5-diamine and 11.2% of other compounds according to analysis by gas chromatography.

We claim:

1. A process for preparing a secondary or tertiary 2-methyl-1,5-pentanediamine of the formula I

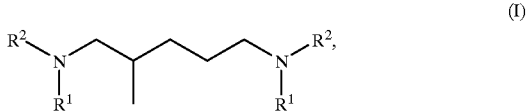

(I)

where

R¹ and R² are H, $C_1$–$C_{20}$-alkyl, $C_3$–$C_8$-cycloalkyl, aryl, $C_7$–$C_{20}$-arylalkyl, where the radicals R¹ and R² may bear substituents selected from the group consisting of $C_1$–$C_{20}$-alkyl, $C_1$–$C_{20}$-alkoxy, $C_6$–$C_{20}$-aryloxy and hydroxy, and R¹ and R² are not simultaneously hydrogen, or R¹ and R² are together an unsubstituted or $C_1$–$C_{20}$-alkyl- and/or $C_1$–$C_{20}$-alkoxy-substituted $C_3$–$C_7$-alkylene chain which may, if desired, be interrupted by one or two O or NR³ groups, where R³ is H or $C_1$–$C_{20}$-alkyl which comprises reacting 2-methylglutarodinitrile with a primary or secondary amine of the formula R¹R²NH and hydrogen at from 50 to 250° C. and pressures of from 0.5 to 35 MPa in the presence of an oxidic supported catalyst comprising one or more noble metals which has been treated with hydrogen at from 50 to 300° C. for at least 0.5 hour before use.

2. A process as claimed in claim 1, wherein the supported catalyst has been treated with hydrogen at from 50 to 300° C. for at least 2 hours before use.

3. A process as claimed in claim 1, wherein the supported catalyst comprises the noble metals palladium and/or platinum and/or ruthenium.

4. A process as claimed in claim 1, wherein the supported catalyst contains from 0.1 to 5% by weight of palladium and from 0.01 to 5% by weight of platinum.

5. A process as claimed in claim 1, wherein the support used for the catalyst is zirconium dioxide or aluminum oxide.

6. A process as claimed in claim 1, wherein the amine used is dimethylamine.

* * * * *